United States Patent
Yasunaga et al.

(10) Patent No.: US 7,492,857 B2
(45) Date of Patent: *Feb. 17, 2009

(54) SELF-ALIGNING SCINTILLATOR-COLLIMATOR ASSEMBLY

(75) Inventors: Takashi Yasunaga, Tokyo (JP); Brian Graves, Waukesha, WI (US); Gerhardt E. Schweinert, Cedarburg, WI (US); Paul Michael Ratzmann, Germantown, WI (US)

(73) Assignee: General Electric Company, Schenectady, NY (US)

( * ) Notice: Subject to any disclaimer, the term of this patent is extended or adjusted under 35 U.S.C. 154(b) by 81 days.

This patent is subject to a terminal disclaimer.

(21) Appl. No.: 11/671,923

(22) Filed: Feb. 6, 2007

(65) Prior Publication Data

US 2007/0140417 A1    Jun. 21, 2007

Related U.S. Application Data (63) Continuation-in-part of application No. 10/711,890, filed on Oct. 12, 2004, now Pat. No. 7,177,387, application No. 11/671,923, filed on Feb. 6, 2007, and a continuation-in-part of application No. 10/324,235, filed on Dec. 19, 2002, now Pat. No. 7,190,759.

(60) Provisional application No. 60/481,722, filed on Nov. 29, 2003.

(51) Int. Cl.
  *H05G 1/64* (2006.01)
  *G21K 1/02* (2006.01)

(52) U.S. Cl. .................... 378/19; 378/98.8; 250/370.09

(58) Field of Classification Search .................... 378/19, 378/98.8, 147, 149, 154; 250/370.09
See application file for complete search history.

(56) References Cited

U.S. PATENT DOCUMENTS

| 5,099,134 | A | 3/1992 | Hase et al. |
| 5,487,098 | A | 1/1996 | Dobbs et al. |
| 5,635,718 | A | 6/1997 | DePuydt et al. |
| 5,668,851 | A | 9/1997 | Dobbs |
| 5,799,057 | A | 8/1998 | Hoffman et al. |
| 5,848,116 | A | 12/1998 | Sugihara |
| 5,955,733 | A | 9/1999 | Orava et al. |
| 6,396,898 | B1 | 5/2002 | Saito et al. |
| 6,424,697 | B1 | 7/2002 | Zastrow et al. |
| 6,426,991 | B1 | 7/2002 | Mattson et al. |
| 6,510,195 | B1 | 1/2003 | Chappo et al. |
| 6,587,538 | B2 * | 7/2003 | Igarashi et al. ................. 378/19 |
| 6,687,334 | B2 | 2/2004 | Galish et al. |
| 6,917,644 | B2 | 7/2005 | Cahn et al. |
| 6,917,664 | B2 | 7/2005 | Chappo et al. |

(Continued)

FOREIGN PATENT DOCUMENTS

NL    1026089    11/2004

*Primary Examiner*—Allen C. Ho
(74) *Attorney, Agent, or Firm*—Ziolkowski Patent Solutions Group, SC (57) ABSTRACT

A CT detector includes a scintillator module including at least one scintillator configured to be impinged with radiographic energy from a radiographic energy source, at least one indexing pin connected to the scintillator module, and a collimator assembly having at least one comb, wherein the collimator assembly defines a relative position of the at least one comb, and wherein the at least one comb has a plurality of teeth configured to engage the at least one indexing pin.

25 Claims, 10 Drawing Sheets

U.S. PATENT DOCUMENTS

| | | |
|---|---|---|
| 6,982,423 B2 | 1/2006 | Eigali |
| 2002/0064252 A1 | 5/2002 | Igarashi et al. |
| 2004/0065465 A1 | 4/2004 | Chappo et al. |
| 2004/0065839 A1 | 4/2004 | Eigali |
| 2004/0120448 A1 | 6/2004 | Ratzmann |
| 2004/0217291 A1 | 11/2004 | Hoge |

* cited by examiner

SELF-ALIGNING SCINTILLATOR-COLLIMATOR ASSEMBLY

CROSS-REFERENCE TO RELATED APPLICATION

The present application is a continuation in part of and claims priority of U.S. patent application Ser. No. 10/711,890 filed Oct. 12, 2004, now U.S. Pat. No. 7,177,387, which claims the benefit of U.S. provisional application Ser. No. 60/481,722, filed Nov. 29, 2003, the disclosure of which is incorporated herein, and also claims priority of U.S. patent application Ser. No. 10/324,235 filed Dec. 19, 2002, now U.S. Pat. No. 7,190,759, the disclosures of which are incorporated herein.

BACKGROUND OF THE INVENTION

The present invention relates generally to diagnostic imaging and, more particularly, to a self-aligning scintillator-collimator assembly and method of manufacturing same.

Typically, in computed tomography (CT) imaging systems, an x-ray source emits a fan-shaped beam toward a subject or object, such as a patient or a piece of luggage. Hereinafter, the terms "subject" and "object" shall include anything capable of being imaged. The beam, after being attenuated by the subject, impinges upon an array of radiation detectors. The intensity of the attenuated beam radiation received at the detector array is typically dependent upon the attenuation of the x-ray beam by the subject. Each detector element of the detector array produces a separate electrical signal indicative of the attenuated beam received by each detector element. The electrical signals are transmitted to a data processing system for analysis which ultimately produces an image.

Generally, the x-ray source and the detector array are rotated about the gantry within an imaging plane and around the subject. X-ray sources typically include x-ray tubes, which emit the x-ray beam at a focal point. X-ray detectors typically include a collimator having a plurality of collimator plates for collimating x-ray beams received at the detector, a scintillator for converting x-rays to light energy adjacent the collimator, and photodiodes for receiving the light energy from the adjacent scintillator and producing electrical signals therefrom.

Typically, each scintillator of a scintillator array converts x-rays to light energy. Each scintillator discharges light energy to a photodiode adjacent thereto. Each photodiode detects the light energy and generates a corresponding electrical signal. The outputs of the photodiodes are then transmitted to the data processing system for image reconstruction.

Image quality can be directly associated with the degree of alignment between the components of the detector. "Crosstalk" between detector cells of a CT detector is common and to some degree is affected by the alignment, or lack thereof, of the detector components. In this regard, cross-talk is typically higher when the components of the CT detector are misaligned.

Cross-talk is generally defined as the communication of data between adjacent cells of a CT detector. Generally, crosstalk is sought to be reduced as cross-talk leads to artifact presence in the final reconstructed CT image and contributes to poor spatial resolution. Typically, four different types of cross-talk may result within a single CT detector. Cross-talk can occur as light from one cell is passed to another through a contiguous layer between the photodiode layer and the scintillator. Electrical cross-talk can occur from unwanted communication between photodiodes. Optical cross-talk may occur through the transmission of light through the reflectors that surround the scintillators. X-ray cross-talk may occur due to x-ray scattering between scintillator cells.

In order to reduce cross-talk, the plates or layers of a collimator are aligned with the cells of the scintillator arrays to very tight and exacting tolerances. This alignment of the plurality of cells of the scintillator array and the plates of the collimator can be a time consuming a labor intensive process. Further, the physical placement or alignment of the collimator to the scintillator array is particularly susceptible to misalignment stack-up. That is, one of the scintillator-collimator assemblies, if unaligned, can detrimentally effect the alignment of adjacent assemblies. Simply, if one collimator-scintillator array combination is misaligned, all subsequently positioned collimator-scintillator array combinations will be misaligned absent implementation of corrective measures. Further, such assemblies require adjusting several detectors when only one of the detectors is misaligned.

Therefore, it would be desirable to design a method and apparatus for the alignment of a collimator and a scintillator module to thereby reduce cross-talk and improve spatial resolution of a final reconstructed image.

BRIEF DESCRIPTION OF THE INVENTION

The present invention is directed to a CT detector and method of manufacturing the same that overcomes the aforementioned drawbacks. The CT detector includes a scintillator module having at least one indexing pin. The indexing pin is constructed to engage a recess between a pair of teeth of a comb designed to align collimating elements of a collimator assembly.

Therefore, according to one aspect of the present invention, a CT detector is disclosed which includes a scintillator module including at least one scintillator configured to be impinged with radiographic energy from a radiographic energy source, at least one indexing pin connected to the scintillator module, and a collimator assembly having at least one comb, wherein the collimator assembly defines a relative position of the at least one comb, and wherein the at least one comb has a plurality of teeth configured to engage the at least one indexing pin.

According to another aspect of the present invention, a scintillator-collimator combination is disclosed which includes a plurality of collimator plates configured to collimate x-rays projected thereat, scintillator module having a scintillator pack formed of a material configured to illuminate upon reception of x-rays, and a comb having a first set of teeth and a second set of teeth, the first set of teeth and the second set of teeth constructed to align the plurality of collimator plates, and the second set of teeth constructed to engage the scintillator module and align the scintillator module relative to the plurality of collimator plates.

In accordance with another aspect of the present invention, a CT system is disclosed that includes a rotatable gantry having a bore centrally disposed therein, a table movable fore and aft through the bore and configured to position a subject for CT data acquisition, a high frequency electromagnetic energy projection source positioned within the rotatable gantry and configured to project high frequency electromagnetic energy toward the subject, and a detector array disposed within the rotatable gantry and configured to detect high frequency electromagnetic energy projected by the projection source and impinged by the subject, the detector array including a plurality of scintillator modules, each having a scintillator array and at least one indexing pin, a collimator assembly having a plurality of collimator plates, and a detector support having at least one comb of alignment teeth, the alignment teeth constructed to align the plurality of collimator plates, and constructed to engage the at least one indexing pin to align a scintillator array with the plurality of collimator plates.

According to yet another aspect of the present invention, a method of manufacturing a CT detector is disclosed which includes providing a scintillator array having at least one locator element extending beyond the scintillator array, providing a comb having a plurality of teeth constructed to define a spacing between collimating elements of a collimator, and positioning the at least one locator element between at least two of the plurality of teeth.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The operating environment of the present invention is described with respect to a four-slice and sixteen slice computed tomography (CT) system. However, it will be appreciated by those skilled in the art that the present invention is equally applicable for use with single-slice or other multi-slice configurations. Moreover, the present invention will be described with respect to the detection and conversion of x-rays. However, one skilled in the art will further appreciate that the present invention is equally applicable for the detection and conversion of other high frequency electromagnetic energy. The present invention will be described with respect to a "third generation" CT scanner, but is equally applicable with other CT systems.

Figure 1:
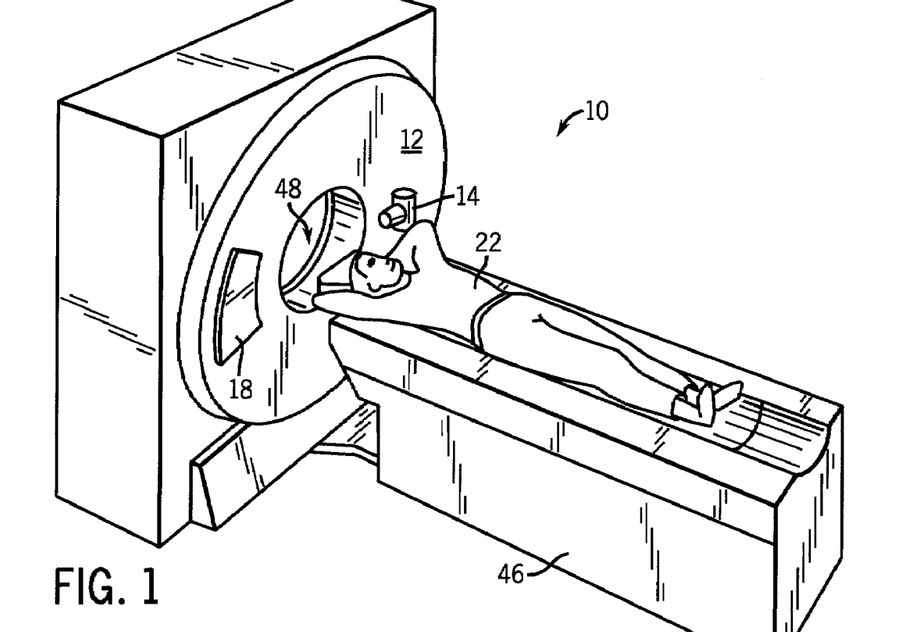
FIG. 1 is a pictorial view of a CT imaging system according to the present invention.
Figure 2:
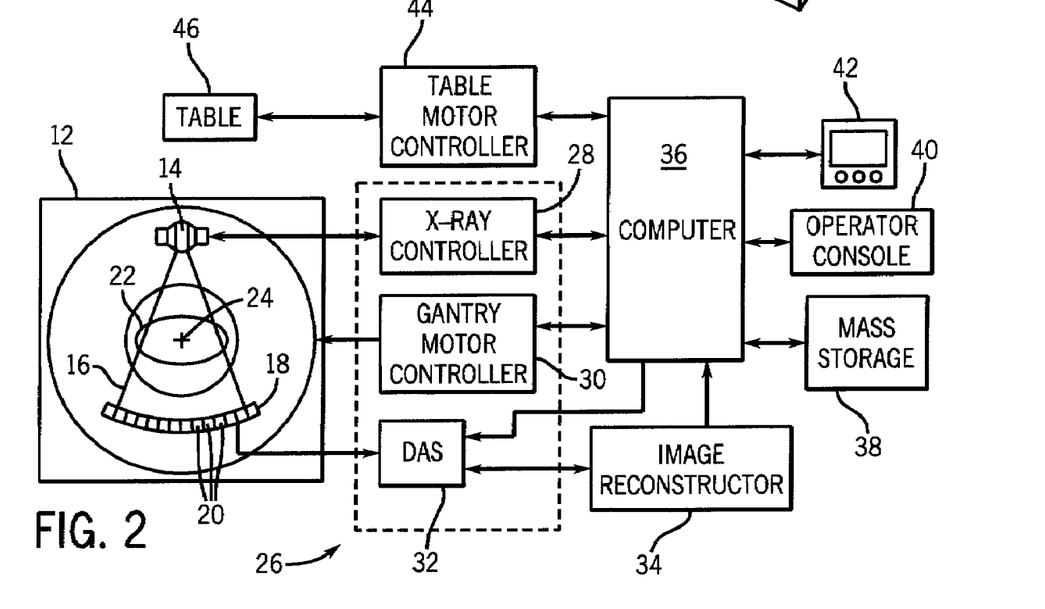
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Figure 3:
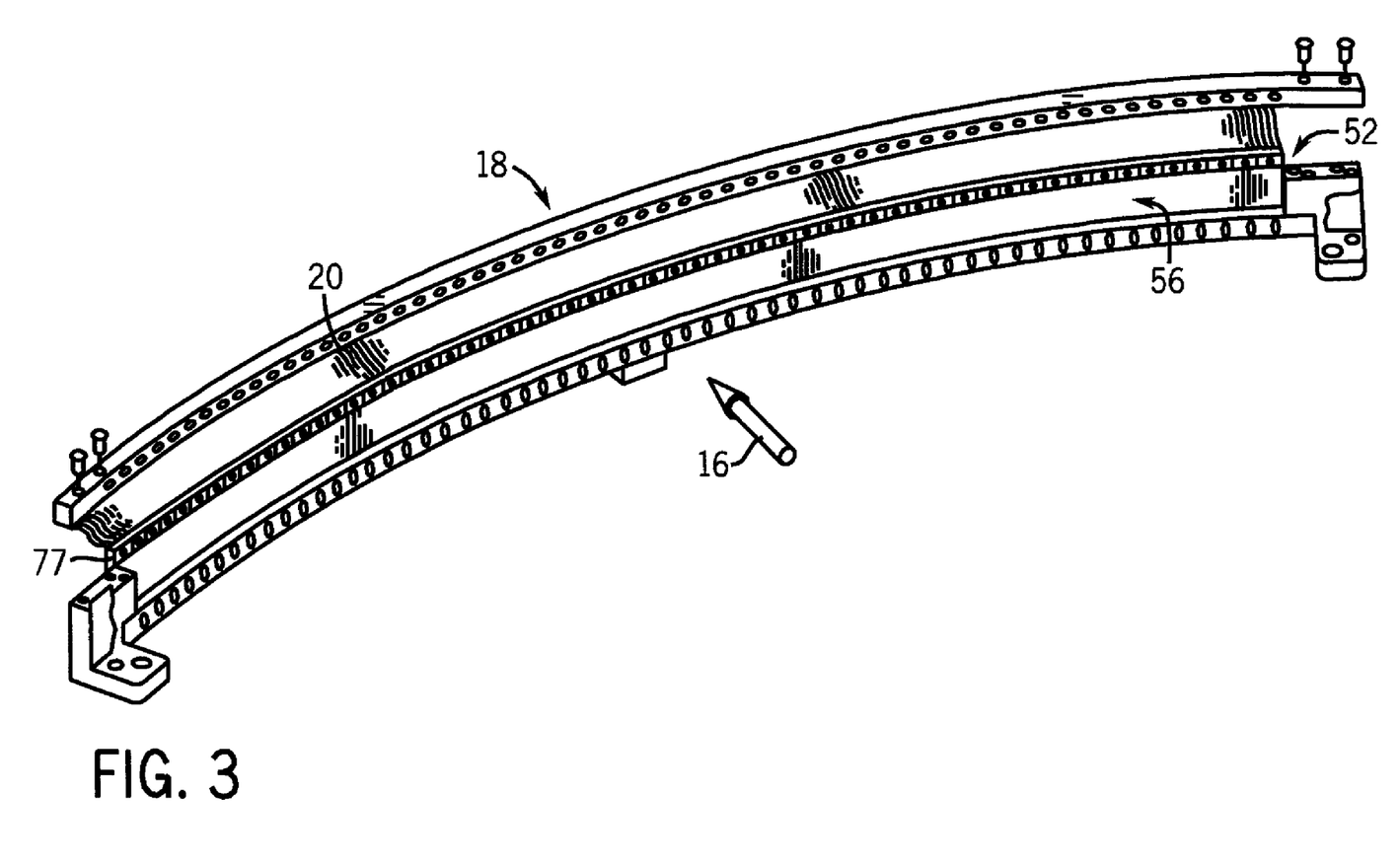
FIG. 3 is a perspective view of one embodiment of a CT system detector array.
Figures 4, 5:
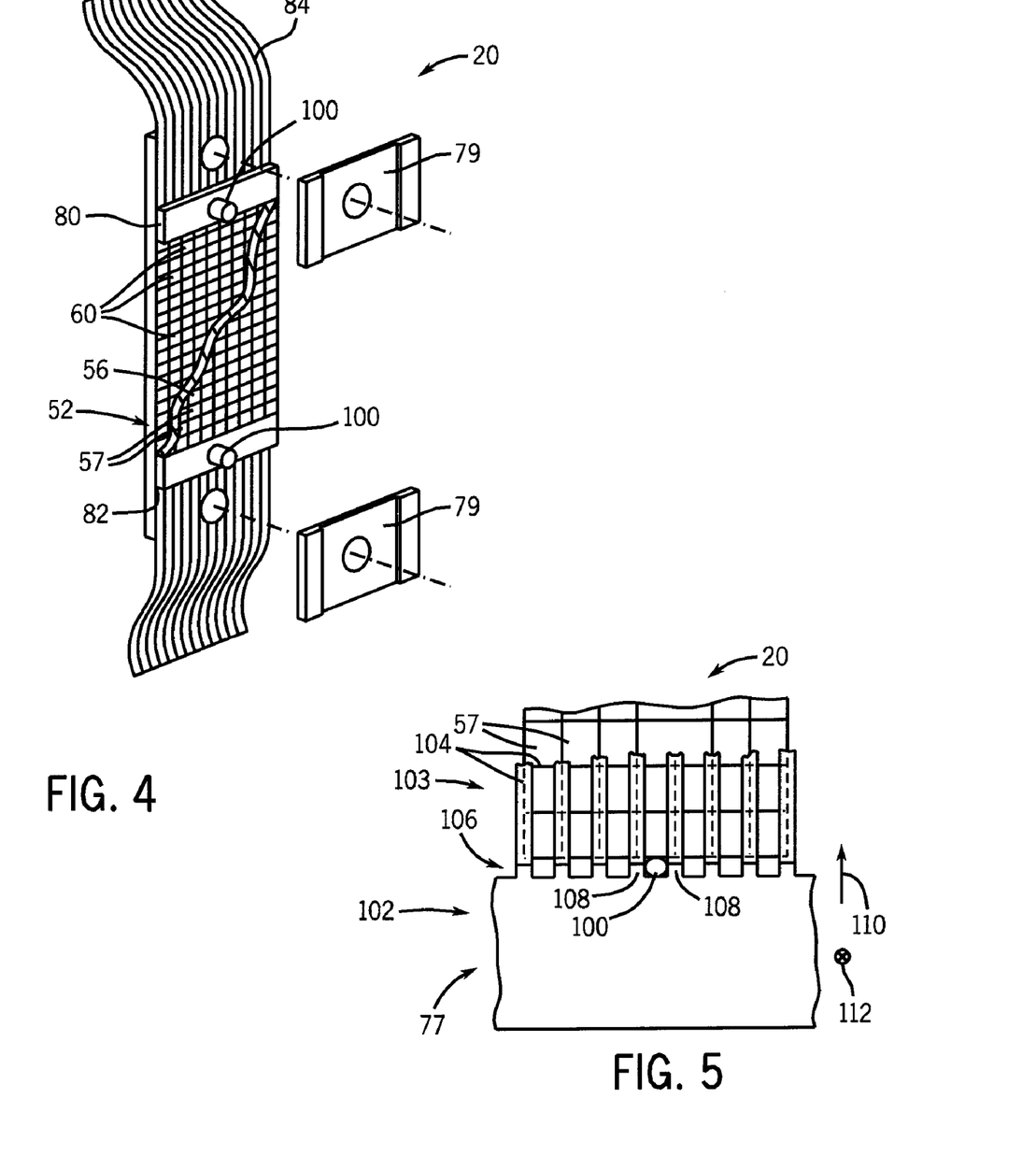
FIG. 4 is a perspective view of one embodiment of a detector of the detector array shown in FIG. 3.
FIG. 5 is a top view of the detector relative to a collimator assembly and detector frame according to the present invention.

As shown in FIGS. 3 and 4, detector array 18 includes a plurality of single scintillator fibers 57 forming a scintillator array 56. In one embodiment, shown in FIG. 3, detector array 18 includes 57 detectors 20, each detector 20 having an array size of 16×16. As a result, array 18 has 16 rows and 912 columns (16×57 detectors) which allows 16 simultaneous slices of data to be collected with each rotation of gantry 12.

Switch arrays 80 and 82, as shown in FIG. 4, are multi-dimensional semiconductor arrays coupled between scintillator array 56 and DAS 32. Switch arrays 80 and 82 include a plurality of field effect transistors (FET) (not shown) arranged as multi-dimensional array. The FET array includes a number of electrical leads connected to each of the respective photodiodes 60 and a number of output leads electrically connected to DAS 32 via a flexible electrical interface 84. Particularly, about one-half of photodiode outputs are electrically connected to switch 80 with the other one-half of photodiode outputs electrically connected to switch 82. Additionally, a thin reflector layer (not shown) may be interposed between each scintillator fiber 57 to reduce light scattering from adjacent scintillators. Each detector 20 is secured to a detector frame 77, FIG. 3, by mounting brackets 79.

Referring to FIG. 4, switch arrays 80 and 82 further include a decoder (not shown) that enables, disables, or combines photodiode outputs in accordance with a desired number of slices and slice resolutions for each slice. Decoder, in one embodiment, is a decoder chip or a FET controller as known in the art. Decoder includes a plurality of output and control lines coupled to switch arrays 80 and 82 and DAS 32. In one embodiment defined as a 16 slice mode, decoder enables switch arrays 80 and 82 so that all rows of the photodiode array 52 are activated, resulting in 16 simultaneous slices of data for processing by DAS 32. Of course, many other slice combinations are possible. For example, decoder may also select from other slice modes, including one, two, and four-slice modes.

Referring to FIG. 5, each detector module 20 is constructed to have a pair of indexing pins 100 that engages a comb 102 integrally formed with or connected to detector frame 77. Comb 102 includes a first set of teeth 106 and a second set of teeth 108. X-rays 16 pass through the plates 104 of collimator assembly 103 and impinge upon scintillators 57. It is understood that comb 102 does not extend over the scintillator array 56 of the detector 20. As such, while comb 102 positions collimator 103 relative to the scintillator array 56, comb 102 does not interfere with the passage of x-rays through the collimator 103 to the scintillator array.

First set of teeth 106 of comb 102 extend in a direction, indicated by arrow 110, and second set of teeth 108 of comb 102 extend in another direction, indicated by arrow 112, generally transverse to direction 110. In this regard, the second set of teeth has a height greater than that of the first set of teeth. As such, the second set of teeth defines a recess sized to snuggly receive an indexing pin 100. Moreover, the spacing between the adjacent teeth of the first set of teeth and the second set of teeth is uniform. This opening defines the direction or gap between the collimator plates. That is, when positioning the collimator plate 104, teeth 106, 108 are used to achieve a uniform alignment and spacing. Plates 104 are generally aligned with the scintillators in order to minimize x-ray cross-talk. It is understood that plates 104 could be constructed to substantially match the construction of different scintillator constructions. These constructions include, but are not limited to, scintillators having generally cellular constructions. Moreover, the collimator plates may extend along the x-axis, z-axis, or both. It is noted that the first set of teeth 106, by extending in direction 110, do not obstruct or interfere with the engagement of indexing pin 100 with second set of teeth 108. Collimator 103 is positioned between detector 20 and x-ray source 16 such that plates 104 are aligned with the scintillators 57 of the scintillator array 56. As such, comb 102 not only defines the spacing between adjacent plates 104, but also aligns the collimator and the scintillator. Although shown as a one-dimensional collimator, it is understood that collimator 103 could be constructed to be a two-dimensional collimator and therefore extend across the scintillator module in both the x and z-directions. Also, while only one comb 102 is shown, it is contemplated that a second comb may also be used to align the collimator plate and scintillator array at each respective end thereof. As such, the scintillator pack may include two indexing pins, aligned with one another, but at opposite ends of the module.

Scintillators 57 of scintillator array 56, particularly for multi-slice detectors, are commonly oriented in two orthogonal dimensions, generally the x and the z-directions. In order to minimize x-ray cross-talk between adjacent scintillators 57, the plates 104 of the collimator are aligned with the scintillators of the scintillator array. The plates of the collimator must also be precisely oriented relative to one another to ensure uniform spacing between adjacent plates. The teeth 106, 108 of comb 102 define a spacing between collimator plates or elements and therefore ensure a precise orientation of each of the plates of collimator 103 relative to each other, and the precise alignment of collimator 103 and scintillator array 56.

Each scintillator array 56 is also indexed to the position of its respective collimator 103 and associated plates 104. This construction reduces stack-up error between adjacent scintillator/collimator arrays resulting from the misalignment of one scintillator/collimator alignment. As such, any stack-up error associated with adjacent scintillator-collimator pairs is significantly reduced.

Another stack-up error is reduced in the assembly of individual scintillators. The indexing pins are positioned relative to the positioning of the scintillator pixels. By positioning the indexing pins relative to the pixels of the scintillator, any stack-up error associated with the relationship between the indexing pins and the scintillator is reduced. As such, serviceability of a detector according to the present invention is improved as the indexing reference points, i.e. the indexing pins and the teeth of the comb, are integrally formed into the components of the device.

Pins 100 are also formed to index the detector 20 to a rail of detector frame 77 as shown in FIG. 5. Such a construction ensures that a plurality of detectors, when attached to the detector frame, will be aligned therewith prior to connection thereto. Such a construction reduces the time required to associate the individual detectors to the frame during the initial assembly and/or during servicing.

Figure 6:
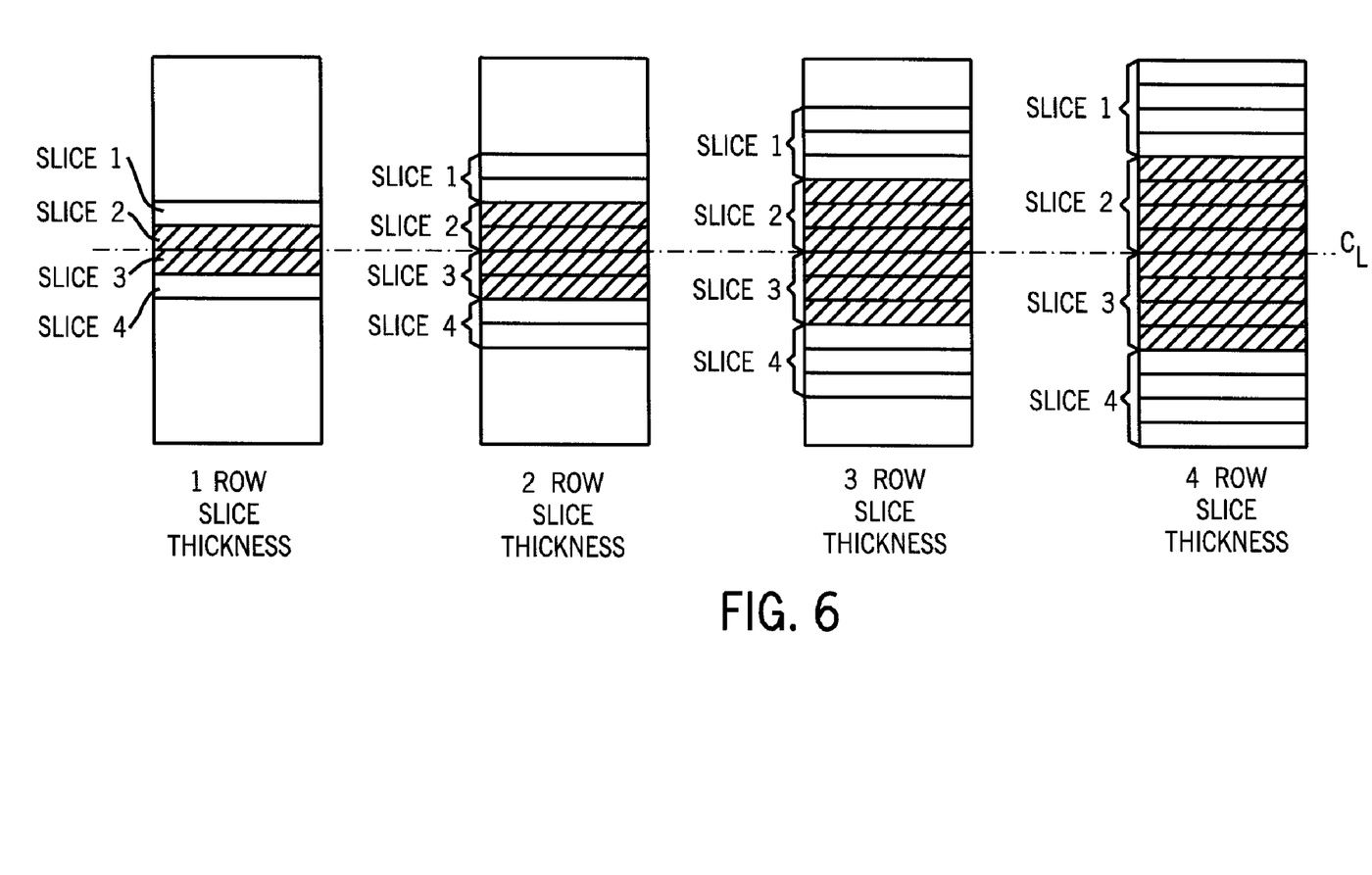
FIG. 6 is illustrative of various configurations of the detector in FIG. 4 in a four-slice mode.

Referring now to FIG. 6, by transmitting the appropriate decoder instructions, switch arrays 80 and 82 can be configured in the four-slice mode so that the data is collected from four slices of one or more rows of photodiode array 52. Depending upon the specific configuration of switch arrays 80 and 82, various combinations of photodiodes 60 can be enabled, disabled, or combined so that the slice thickness may consist of one, two, three, or four rows of scintillator array elements 57. Additional examples include, a single slice mode including one slice with slices ranging from 1.25 mm thick to 20 mm thick, and a two slice mode including two slices with slices ranging from 1.25 mm thick to 10 mm thick. Additional modes beyond those described are contemplated.

Figure 7:
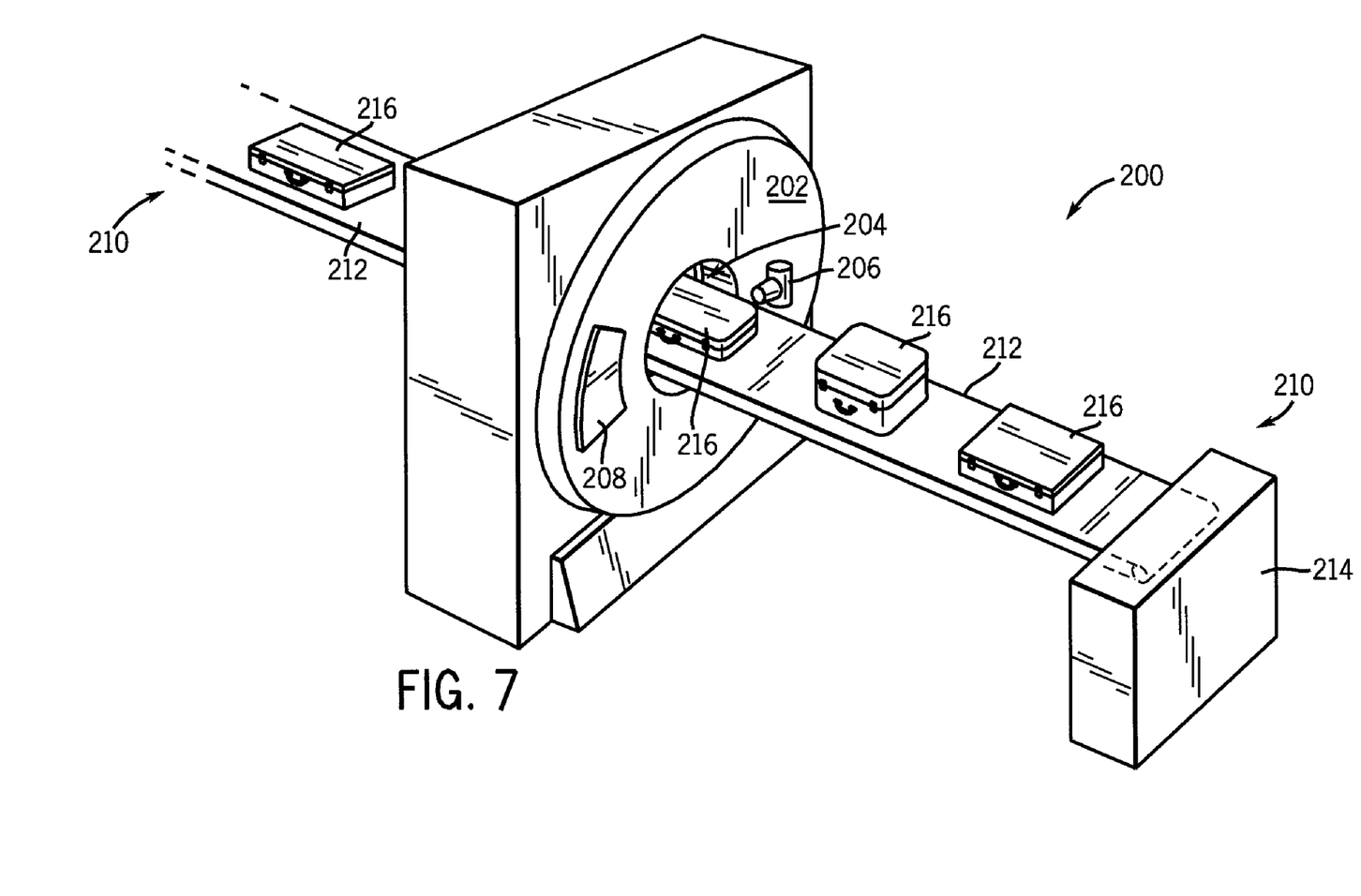
FIG. 7 is a pictorial view of a CT system for use with a non-invasive package inspection system.

Referring now to FIG. 7 package/baggage inspection system 200 includes a rotatable gantry 202 having an opening 204 therein through which packages or pieces of baggage 216 may pass. The rotatable gantry 202 houses a high frequency electromagnetic energy source 206 as well as a detector assembly 208 having scintillator arrays comprised of scintillator cells similar to that shown in FIG. 6. A conveyor system 210 is also provided and includes a conveyor belt 212 supported by structure 214 to automatically and continuously pass packages or baggage pieces through opening to be scanned. Objects are fed through opening by conveyor belt 212, imaging data is then acquired, and the conveyor belt 212 removes the packages 216 from opening 204 in a controlled and continuous manner. As a result, postal inspectors, baggage handlers, and other security personnel may non-invasively inspect the contents of packages 216 for explosives, knives, guns, contraband, etc.

Figure 8:
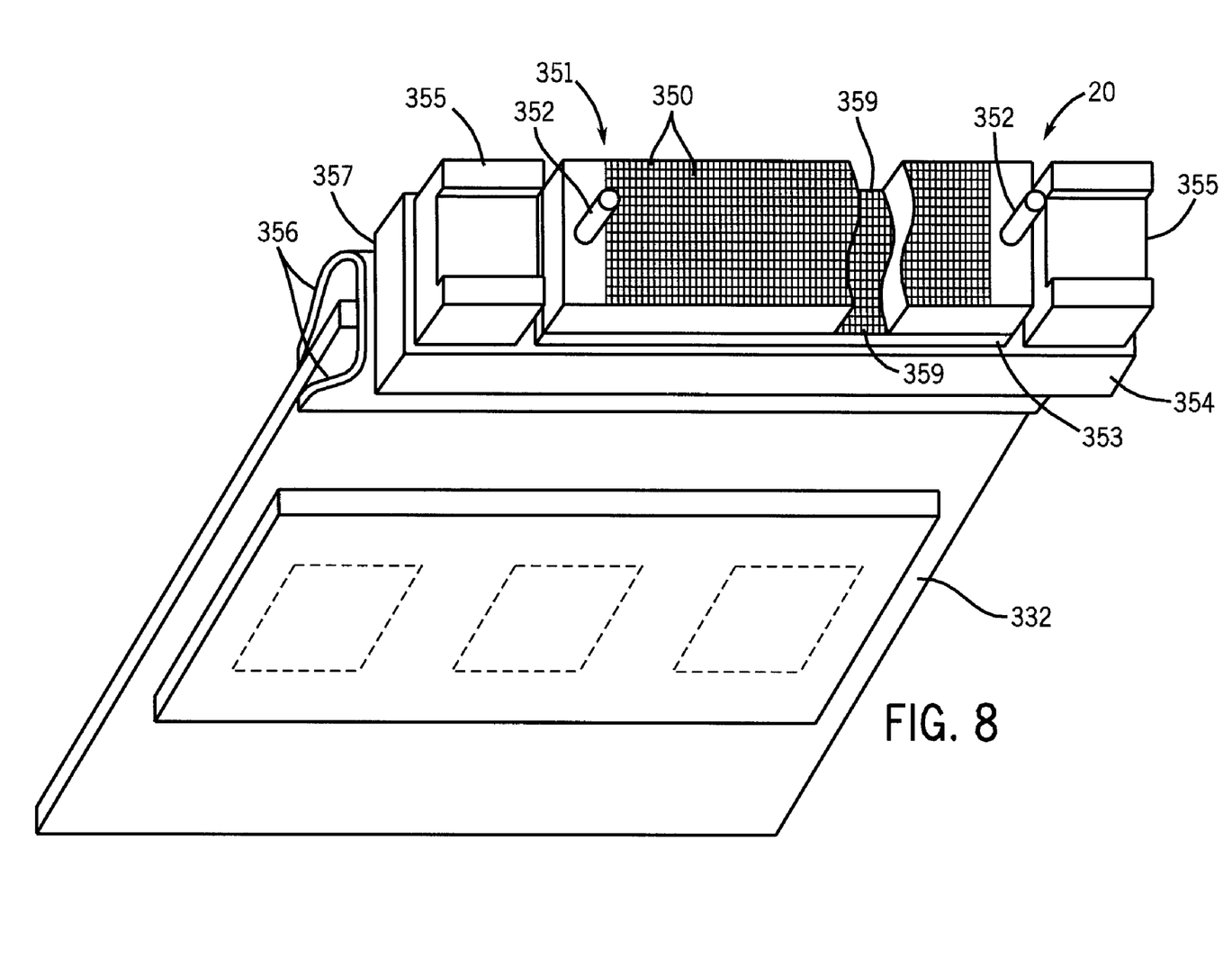
FIG. 8 is a perspective view of one embodiment of a detector according to an embodiment of the present invention.

Referring to FIG. 8, an alternate embodiment includes detector 20 assembled together with DAS 332. Each detector 20 includes a number of detector elements 350 arranged in pack 351. Detector 20 includes pins 352 positioned within pack 351 relative to detector elements 350. Pack 351 is positioned on a backlit diode array 353 having a plurality of diodes 359. Backlit diode array 353 is in turn positioned on multi-layer substrate 354. Spacers 355 are positioned on multi-layer substrate 354. Detector elements 350 are optically coupled to backlit diode array 353, and backlit diode array 353 is in turn electrically coupled to multi-layer substrate 354. Flex circuits 356 are attached to face 357 of multi-layer substrate 354 and to DAS 332. Detector 20 is positioned within detector assembly 18 of FIGS. 1-3 by use of pins 352.

Figure 9:
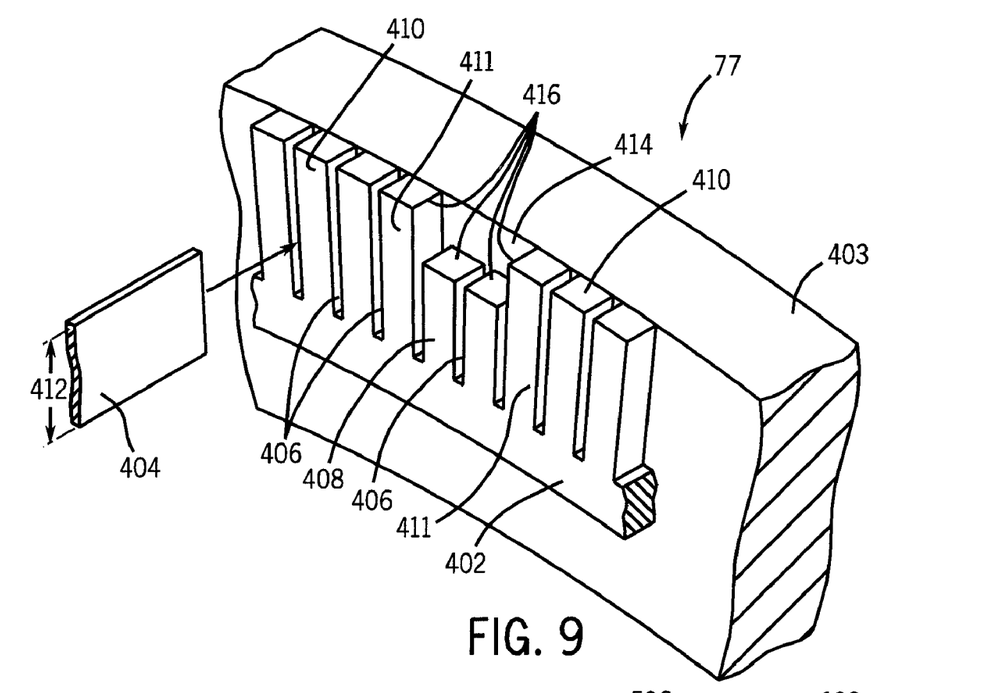
FIG. 9 is a partial perspective view of a rail and comb configured to receive a detector, such as that shown in FIG. 8, therein according to an embodiment of the present invention.

FIG. 9 illustrates a portion of detector frame 77 of FIGS. 3 and 5 having comb 402 positioned on a rail 403. Comb 402 includes a plurality of teeth having a first length 408 and having a second length 410 forming gaps 406 into which plates 404 are positioned. Accordingly, a clearance region 414 is formed that is bounded in part by surfaces 416 of teeth 408 and two neighboring teeth 411. Plate width 412 is less than the length of teeth 408, such that when plates 404 are positioned within gaps 406, plate 404 does not obstruct clearance region 414. Plates 404 are generally aligned with the scintillators such as for instance detector elements 350 of detector 20, in order to minimize x-ray cross-talk therein. It is understood that plates 404 could be constructed to substantially match the construction of different scintillator constructions. These constructions include, but are not limited to, scintillators having generally cellular constructions.

Detector frame 77 of FIGS. 3 and 5, in an embodiment of the present invention, is formed having two opposing rails 403 as shown in FIG. 9, each having combs 402 positioned thereon and substantially mirroring one another, thus forming a collimator, one embodiment of which is illustrated as collimator assembly 103 of FIG. 5. Clearance regions 414 of each of the opposing rails 403 form positioning locations for pins 352 of detector 20 of FIG. 8. As such, combs 402 having teeth 408, 410 of opposing rails 403, serve the dual purpose of providing gaps 406 for mounting plates 404, and providing clearance region 414 and surfaces such as on teeth 411 for engaging, flanking, or abutting positioning pins 352 of module assembly 20 of FIG. 8. This construction reduces stack-up error between adjacent scintillator/collimator arrays resulting from the misalignment of scintillator with respect to collimator plates. As such, any stack-up error associated with adjacent scintillator-collimator pairs is significantly reduced. Accordingly, combs 402, typically fabricated by etching or wire EDM and the like, provide accurate and precise relative locations between plates 404 and detector elements 350 as in, for instance, module 20 of FIG. 8, when module 20 is positioned on detector frame 77.

Another stack-up error is reduced in the assembly of individual scintillators. The indexing pins are positioned relative to the positioning of the scintillator pixels. By positioning the indexing pins relative to the pixels of the scintillator, stack-up error associated with the relationship between the indexing pins and the scintillator is reduced. As such, serviceability of a detector within a CT system according to the present invention is improved as the indexing reference points, i.e. the indexing pins and the teeth of the comb, are integrally formed into the components of the device.

Figure 10:
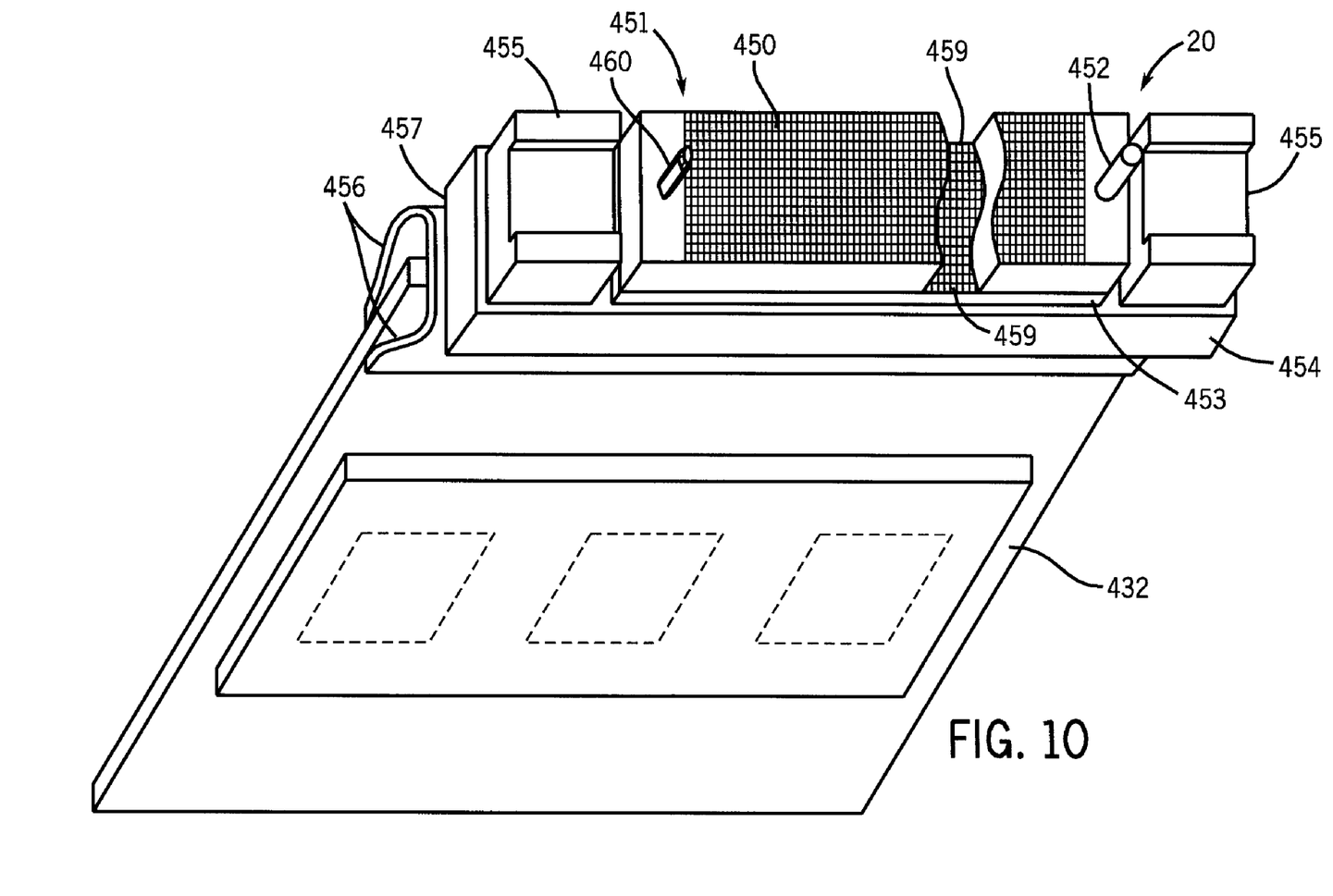
FIG. 10 is a perspective view of a detector according to an other embodiment of the present invention.

Referring to FIG. 10, detector 20 of FIGS. 1-3 in an alternate embodiment includes DAS 432, with each detector 20 including a number of detector elements 450 arranged in pack 451. Detectors 20 include cylindrical pin 452 and diamond-shaped pin 460 positioned within pack 451 relative to detector elements 450. Diamond-shaped pin 460, in an alternative embodiment, is a hexagonally-shaped pin having a tapered top section. Pack 451 is positioned on a backlit diode array 453 having a plurality of diodes 459. Backlit diode array 453 is in turn positioned on multi-layer substrate 454. Spacers 455 are positioned on multi-layer substrate 454. Detector elements 450 are optically coupled to backlit diode array 453, and backlit diode array 453 is in turn electrically coupled to multi-layer substrate 454. Flex circuits 456 are attached to face 457 of multi-layer substrate 454 and to DAS 432. Detectors 20 are positioned within detector assembly 18 of FIGS. 1-3 by use of pins 452.

Figure 11:
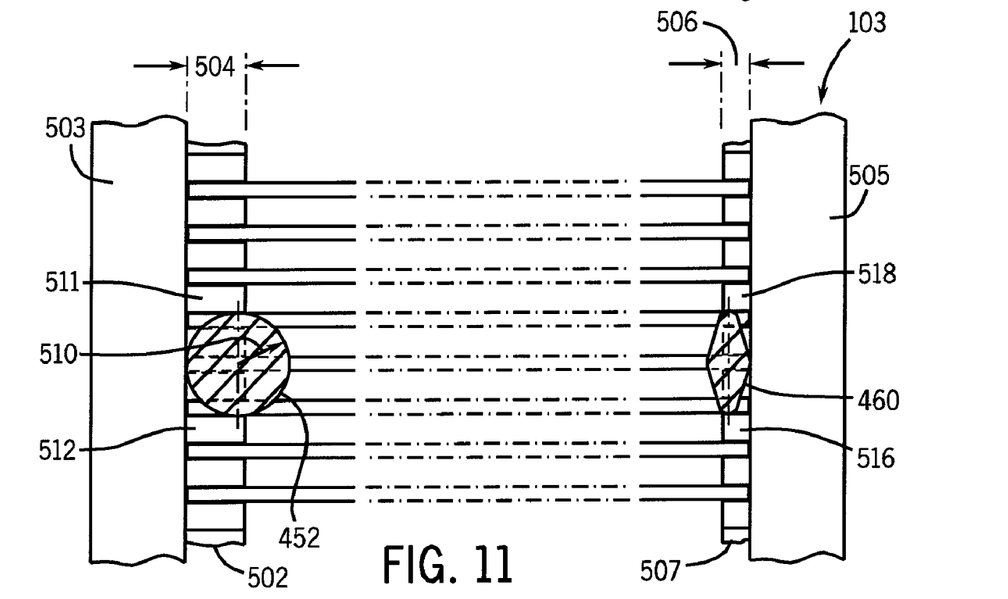
FIG. 11 is a partial plan view of rails and plates illustrating pin placement on a collimator assembly according to an embodiment of the present invention.

Diamond-shaped pin 460 of FIG. 10 has a lower profile than cylindrical pin 452, thus enabling a more shallow comb to provide locating features for module 20. This is best illustrated in FIG. 11, which is a plan view of collimator assembly 103, showing only cylindrical pin 452 and diamond-shaped pin 460 of module 20 as mounted in collimator assembly 103. Collimator assembly 103 is formed having opposing rails 503, 505. In this embodiment, a first comb 502 has a first depth 504 and is positioned against rail 503. Cylindrical pin 452 of module 20 of FIG. 10 is thereby positioned between two teeth of comb 502, such as teeth 511, 512. First depth 504 is greater than radius 510 of pin 452, thus ensuring engagement of pin 452 with teeth 511 and 512, when module 20 is positioned in collimator assembly 103. A second comb 507, having a second depth 506 that is shallower than first depth 504 of comb 502, is positioned against second rail 505. Accordingly, diamond-shaped pin 460 of module 20 of FIG. 10 thus engages teeth 516 and 518 of comb 507. As such, the use of diamond-shaped pin 460 enables a narrower comb 507 than does a comparable comb 502 constructed to engage a cylindrical pin, such as cylindrical pin 452.

Each row/array of detector elements 18 in this invention comprises a plurality of detector modules 20, wherein each detector module 20 comprises all the relevant detector components (i.e., diodes, scintillator packs, collimators, etc.) in a single pre-assembled assembly, which may then be easily positioned within CT imaging system 10. The present invention comprises systems and methods that allow these CT radiation detector modules 20 to be very accurately and easily assembled. These detector modules 20 comprise a support structure 652 and spacers 656 that allow all the detector components to be assembled together into a single assembly that can then be easily aligned and inserted into a CT imaging system 10. This invention utilizes pins 655 in the spacers 656 (i.e., the pin/spacer assembly) as the reference points upon which all other detector module components (i.e., diodes, scintillator packs, collimators, etc.) are aligned, thereby allowing for easy and precise placement of all detector components. This pin-based support structure has many advantages: (1) the pins provide parallel surfaces for mounting the detector module components upon; (2) the pins allow the detector module to be precisely positioned and aligned in a CT imaging system; (3) the pins provide optical and mechanical reference features for positioning the diode and scintillator pack(s) during assembly of the detector modules; (4) the pins provide a precise mechanical location where a post-patient collimator may be attached thereto; and (5) the pins allow the detector modules to be mechanically aligned and attached to the final CT imaging system (i.e., via elongated slots in the support rails in some current CT imaging systems).

Figure 12:
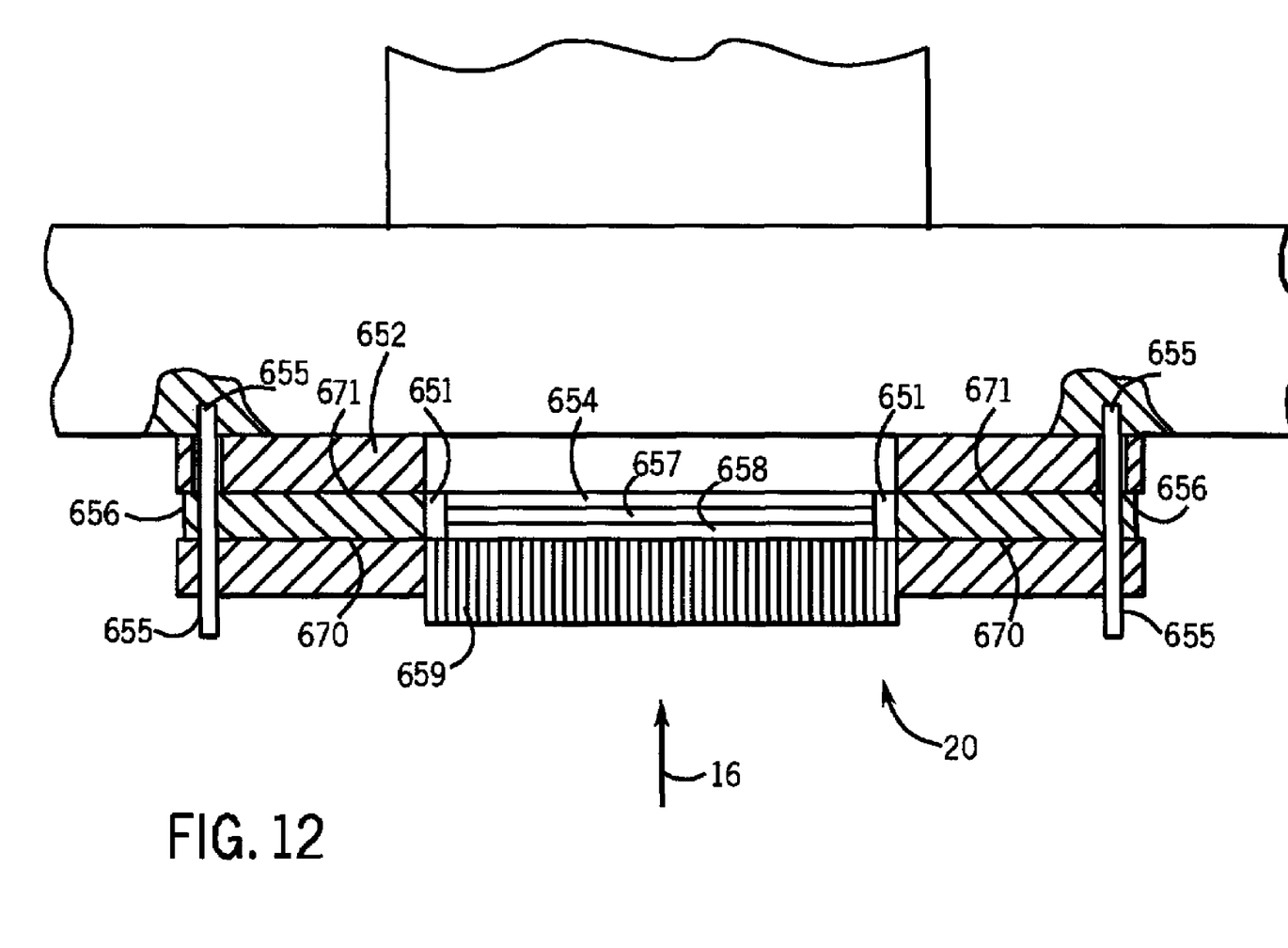
FIG. 12 is a side view showing basic components of a detector and an assembly fixture utilized in embodiments of this invention.

A side view of a detector module 20 as assembled in one embodiment of this invention is shown in FIG. 12. In this particular embodiment, the detector module 20 comprises the following components: a support structure 652, an electronic flex connector 654, two pins 655, two spacers 656, diodes 657, two scintillator packs 658, and a collimator assembly 659.

Figure 13:
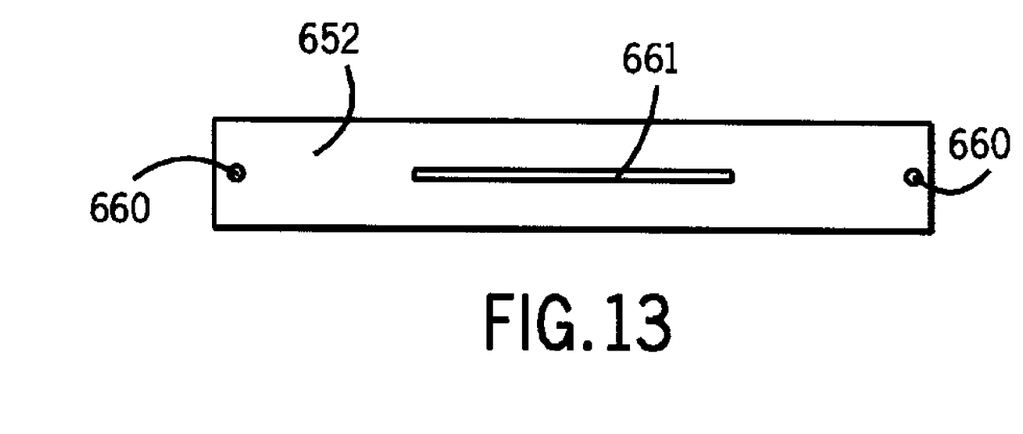
FIG. 13 is a top view of a support structure utilized in embodiments of this invention.
Figure 14:
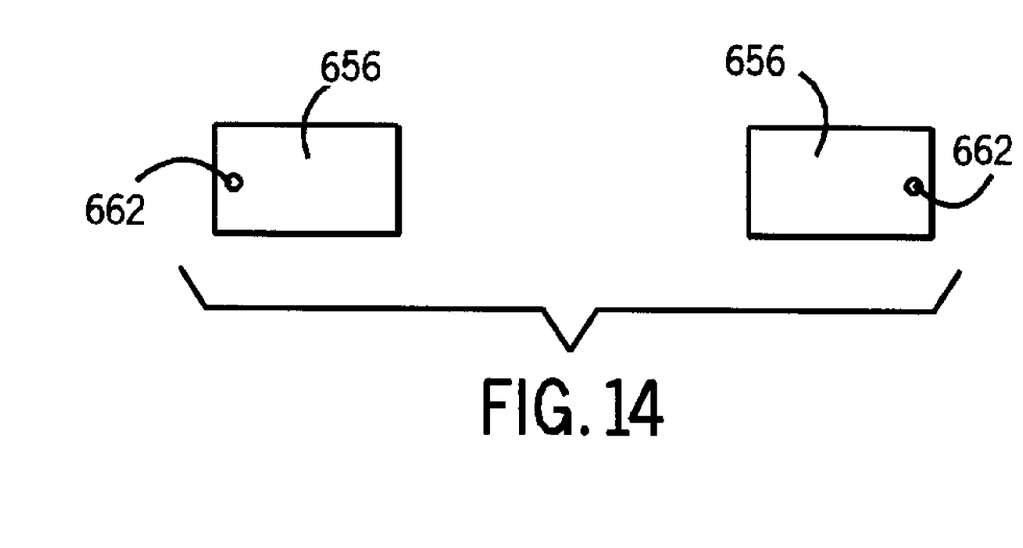
FIG. 14 is a top view of the spacers utilized in embodiments of this invention.

In embodiments, the support structure 652 for the detector modules 20 may be made of any suitable high stiffness material, such as for example, compression molded carbon fiber. As shown in FIG. 13, the support structure 652 preferably comprises a rectangular shaped piece of material having an elongated slot 661 in its central portion and apertures 660 proximate each end. The final support structure also comprises two spacers 656, as shown in FIG. 14. Each spacer 656 may be made of any suitable material, and preferably comprises an aperture 662 proximate one end where a pin 655 may be inserted. The pins 655 on the spacer/pin assemblies provide the reference points against which all other components of the detector module 20 will be aligned during assembly. As such, the top 670 and bottom 671 surfaces of each spacer 656 preferably have tight flatness and co-planarity requirements. Furthermore, the pins 655 preferably have tight diameter requirements and, when pressed into the spacers 656, have tight perpendicularity requirements with the top 670 and bottom 671 surfaces of the spacers 656.

Preferably, the detector modules 20 are assembled in an assembly fixture so that the detector components can be precisely and accurately assembled and attached to one another. For example, the pins 655 may extend from the spacers 656 through the support structure 652 and into precisely located apertures in the assembly fixture.

In embodiments, support structure 652 may be inserted into the assembly fixture. Next, the pins 655 may be inserted into the apertures 662 in spacers 656, which may comprise press-fitting the pins 655 into slightly smaller apertures 662 in spacers 656. The spacer/pin assemblies may then be bonded or otherwise attached to support structure 652 in any suitable manner. Once the spacers 656, pins 655 and support structure 652 are assembled, the free end of the electronic flex connector 654, which preferably has its other end bonded or otherwise attached to the back surface of diodes 657, may then be fed through the elongated slot 661 in support structure 652. Diodes 657 are the active portion of the detector module 20. The free end of electronic flex connector 654 carries the electrical signals from the diodes 657 to the read-out chips in a data acquisition system in a manner well know in the industry. The diodes 657 (i.e., the back-bonded diodes in this embodiment) may be aligned relative to the assembly fixture and support structure 652 in any suitable manner, such as by optically or mechanically aligning features on the top of the diodes 657 to the pins 655, and then the flex connector/diode assembly may be attached to the support structure 652 in any suitable manner. Scintillator packs 658 may then be aligned relative to the assembly fixture and support structure 652 in any suitable manner, such as by optically or mechanically aligning features on the top of the scintillator packs 658 to the pins 655, and the scintillator packs 658 may then be optically coupled to the diodes 657 in any suitable manner, such as by bonding or gluing. The scintillator packs 658 detect the x-rays, and then convert the x-rays into photons (i.e., visible light) that can be detected by the diodes 657. Thereafter, in embodiments, a collimator assembly 659 that was specifically designed to align off pins 655 may be aligned with and operatively coupled to detector module 20 in any suitable manner, such as by placing precisely-located apertures in the collimator assembly over the pins 655. The collimator assembly 659 shapes the detected x-rays to the focal spots of the detectors so as to reduce the scattered radiation caused by off-focal alignment. Gaps 651 may be present between the spacers 656 and the active portion of the detector module 20 (i.e., the active portion of the detector module comprises the electronic flex connector 654, the diodes 657 and the scintillator packs 658).

The completed detector module assembly 20 preferably has pins 655 protruding beyond the surface of the collimator assembly 659 so that the detector module 20 can be assembled directly into the CT imaging system 10, preferably via a precisely-located slot on the support rail(s) of the CT imaging system 10 into which pins 655 may be inserted. In this manner, there should be no need to adjust alignment of the detector module 20 with the support rails, since the diameter of each pin 655 is preferably only a few microns smaller than the slot(s) on the support rails. While the other ends of pins 655 are shown extending beyond the surface of the support structure 652, this may or may not be necessary, depending on the particular CT imaging system the detector module 20 will be attached to.

As described above, the systems and methods of the present invention allow the detector elements in CT imaging systems to be accurately and more easily assembled than currently possible. Advantageously, the modular pin-based design of these support structures provides for the simple alignment of all relevant components (i.e., diode, scintillator packs, collimator, etc.) to the same pin(s), which is utilized as a local reference point for the entire detector module. Additionally, this design is easily and continuously extensible in the Z-direction, allowing additional rows of detector modules to be added to lengthen the coverage in the Z-direction. This invention allows each successive row of detector modules to be positioned close enough to one another so that gaps in Z-coverage are avoided. This is particularly advantageous since the medical industry now desires to have longer Z-coverage so that they can get more coverage of a patient with each rotation of the gantry, thereby allowing full organ imaging in a single CT scan.

Therefore, according to one embodiment of the present invention, a CT detector includes a scintillator module including at least one scintillator configured to be impinged with radiographic energy from a radiographic energy source, at least one indexing pin connected to the scintillator module, and a collimator assembly having at least one comb, wherein the collimator assembly defines a relative position of the at least one comb, and wherein the at least one comb has a plurality of teeth configured to engage the at least one indexing pin.

According to another embodiment of the present invention, a scintillator-collimator combination includes a plurality of collimator plates configured to collimate x-rays projected thereat, scintillator module having a scintillator pack formed of a material configured to illuminate upon reception of x-rays, and a comb having a first set of teeth and a second set of teeth, the first set of teeth and the second set of teeth constructed to align the plurality of collimator plates, and the second set of teeth constructed to engage the scintillator module and align the scintillator module relative to the plurality of collimator plates.

In accordance with another embodiment of the present invention, a CT system includes a rotatable gantry having a bore centrally disposed therein, a table movable fore and aft through the bore and configured to position a subject for CT data acquisition, a high frequency electromagnetic energy projection source positioned within the rotatable gantry and configured to project high frequency electromagnetic energy toward the subject, and a detector array disposed within the rotatable gantry and configured to detect high frequency electromagnetic energy projected by the projection source and impinged by the subject, the detector array including a plurality of scintillator modules, each having a scintillator array and at least one indexing pin, a collimator assembly having a plurality of collimator plates, and a detector support having at least one comb of alignment teeth, the alignment teeth constructed to align the plurality of collimator plates, and constructed to engage the at least one indexing pin to align a scintillator array with the plurality of collimator plates.

According to yet another embodiment of the present invention, a method of manufacturing a scintillator module is disclosed which includes providing a scintillator array having at least one locator element extending beyond the scintillator array, providing a comb having a plurality of teeth constructed to define a spacing between collimating elements of a collimator, and positioning the at least one locator element between at least two of the plurality of teeth.

The present invention has been described in terms of the preferred embodiment, and it is recognized that equivalents, alternatives, and modifications, aside from those expressly stated, are possible and within the scope of the appending claims.

What is claimed is:

1. A CT detector comprising:
    a scintillator module including at least one scintillator configured to be impinged with radiographic energy from a radiographic energy source;
    at least one indexing pin connected to the scintillator module; and
    a collimator assembly having at least one comb, wherein the collimator assembly is configured to position the at least one comb, and wherein the at least one comb has a plurality of teeth configured to engage the at least one indexing pin.

2. The CT detector of claim 1 wherein the at least one indexing pin further comprises at least one diamond-shaped pin.

3. The CT detector of claim 1 wherein the plurality of teeth are further configured to position a plurality of collimator plates.

4. The CT detector of claim 1 wherein the plurality of teeth have a first set of teeth extending a first length and a second set of teeth extending a second length, wherein the second set of teeth is longer than the first set of teeth.

5. The CT detector of claim 4 wherein the second set of teeth are constructed to flank the at least one indexing pin.

6. The CT detector of claim 5 wherein the at least one indexing pin is generally flanked by at least two teeth of the second set of teeth, and has a side surface constructed to abut a side surface of the second set of teeth.

7. The CT detector of claim 1 wherein the at least one scintillator includes a plurality of scintillators uniformly arranged in a scintillator array.

8. The CT detector of claim 1 incorporated into a rotatable gantry of a CT imaging system which is extensible in the Z-direction.

9. A scintillator-collimator combination comprising:
    a plurality of collimator plates configured to collimate x-rays projected thereat;
    a scintillator module having a locating pin and a scintillator pack formed of a material configured to illuminate upon reception of x-rays; and
    a comb having a first set of teeth and a second set of teeth, the first set of teeth and the second set of teeth constructed to align the plurality of collimator plates, and the second set of teeth constructed to engage the locating pin on the scintillator module and align the scintillator module, via the locating pin, relative to the plurality of collimator plates.

10. The scintillator-collimator combination of claim 9 wherein the locating pin is constructed to snuggly engage a recess of the comb, wherein the recess is defined between a pair of the second set of teeth.

11. The scintillator-collimator combination of claim 9 wherein the locating pin has a diamond shape.

12. The scintillator-collimator combination of claim 9 wherein the locating pin is configured to align the scintillator pack with respect to the plurality of collimator plates.

13. The scintillator-collimator combination of claim 9 further comprising a photodiode array, wherein the scintillator pack is configured to be optically coupled to the photodiode array and configured to detect illumination from the scintillator pack and output electrical signals responsive thereto.

14. The scintillator-collimator combination of claim 9 incorporated into a CT imaging system designed to acquire diagnostic data of a medical patient.

15. A scintillator-collimator combination comprising:
    a plurality of collimator plates configured to collimate x-rays projected thereat;
    a scintillator module having:
        a scintillator pack formed of a material configured to illuminate upon reception of x-rays; and
        at least one locating pin; and
    a comb having a first set of teeth and a second set of teeth, the first set of teeth and the second set of teeth constructed to align the plurality of collimator plates, and the second set of teeth constructed to engage the scintillator module and align the scintillator module relative to the plurality of collimator plates;
    wherein the comb comprises a recess defined between a pair of the second set of teeth, and
    wherein the at least one locating pin is constructed to snuggly engage the recess.

16. The scintillator-collimator combination of claim 15 wherein the locating pin has a diamond shape.

17. The scintillator-collimator combination of claim 15 wherein the locating pin is configured to align the scintillator pack with respect to the plurality of collimator plates.

18. A CT system comprising:
    a rotatable gantry having a bore centrally disposed therein;
    a table movable fore and aft through the bore and configured to position a subject for CT data acquisition;
    a high frequency electromagnetic energy projection source positioned within the rotatable gantry and configured to project high frequency electromagnetic energy toward the subject; and
    a detector array disposed within the rotatable gantry and configured to detect high frequency electromagnetic energy projected by the projection source, the detector array including:
        a plurality of scintillator modules, each having a scintillator array and at least one indexing pin;
        a collimator assembly having a plurality of collimator plates; and
        a detector support having at least one comb of alignment teeth, the alignment teeth constructed to align the plurality of collimator plates, and the alignment teeth constructed to engage the at least one indexing pin to align a scintillator array with the plurality of collimator plates.

19. The CT system of claim 18 wherein the at least one comb includes a first set of teeth extending a first length and a second set of teeth extending a second length, wherein the second set of teeth is longer than the first set of teeth.

20. The CT system of claim 19 wherein the comb defines a uniform spacing between collimator plates of the plurality of collimator plates.

21. The CT system of claim 19 wherein the second set of teeth extends beyond an edge of the collimator plates.

22. The CT system of claim 19 wherein the second set of teeth flank the at least one indexing pin.

23. The CT system of claim 18 wherein the at least one indexing pin is hexagonally-shaped with a tapered top section.

24. The CT system of claim 18 wherein the at least one indexing pin is laterally positioned beyond an end of a respective scintillator array.

25. A method of manufacturing a CT detector comprising the steps of:
providing a scintillator array having at least one locator element extending beyond the scintillator array;
providing a comb having a plurality of teeth constructed to define a spacing between collimating elements of a collimator; and
positioning the at least one locator element between at least two of the plurality of teeth.

* * * * *